United States Patent
Flynn et al.

(10) Patent No.: US 6,743,055 B1
(45) Date of Patent: Jun. 1, 2004

(54) ADAPTER INTEGRATED INTO A LEAD BODY

(75) Inventors: David M. Flynn, Lino Lakes, MN (US); Stuart R. Chastain, Shoreview, MN (US); Steve Hahn, Shoreview, MN (US); June M. Zytkovicz, Mounds View, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 763 days.

(21) Appl. No.: 09/139,155

(22) Filed: Aug. 24, 1998

(51) Int. Cl.$^7$ ............................................. H01R 25/00
(52) U.S. Cl. ...................................... 439/651; 439/909
(58) Field of Search ...................... 607/37, 2, 9, 115, 607/116; 439/909, 651, 652, 175

(56) References Cited

U.S. PATENT DOCUMENTS 5,222,506 A    6/1993  Patrick et al.
5,413,595 A  * 5/1995  Stutz, Jr. .................... 607/637
5,679,026 A   10/1997  Fain et al.

* cited by examiner

Primary Examiner—Ross Gushi
(74) Attorney, Agent, or Firm—Thomas J. Nikolai; Nikolai & Mersereau, P.A.

(57) ABSTRACT

A lead having an adapting member extending from the lead's main body, wherein the adapting member is suitable for receiving a terminal pin of a second lead thereby electrically coupling the second lead thereto. The lead may then be electrically and mechanically coupled to a single electrical port of a medical device. The lead may be unipolar, bipolar, or multipolar and suitable for use with a pacer, defibrillator or other cardiac rhythm management device, wherein the second lead is electrically connected in parallel with a selected conductor of the lead. The adapter may be positioned on the lead adjacent the terminal pin such that when the lead is coupled to the medical device the adapter engages a portion of the medical device.

11 Claims, 8 Drawing Sheets

ADAPTER INTEGRATED INTO A LEAD BODY

BACKGROUND OF THE INVENTION

I. Field of the Invention

This invention relates generally to pacing defibrillation and hybrid lead wires that are connectable to an implantable cardiac rhythm management device, and more particularly relates to a lead design that electrically and mechanically couples two leads to a single port in a header assembly of the implantable device. The lead may be unipolar, bipolar or multipolar and includes an adapting member formed within the lead body, wherein a port is formed in the adapting member suitable for receiving a terminal end of an additional lead. The lead of the present invention is adaptable as a pacing, defibrillation, or hybrid pacing/defibrillation lead.

II. Discussion of the Related Art

A cardiac rhythm management device capable of pacing or defibrillating a patient's heart typically includes a pulse generator having an electronic circuit and power supply contained to within a metal casing, commonly referred to as "the can". A lead, capable of transmitting a therapeutic electrical signal generated by the pulse generator to the heart, is electrically coupled to the electronic circuit of the pulse generator. A "header" having a receptacle or port is commonly provided in order to "plug" the lead into the rhythm management device and electrically couple the lead to the electronic circuit contained within the can. Over the years, the receptacles located in the header of the implantable cardiac rhythm management device and the terminal connector end of a corresponding lead have been standardized by the International Standards Organization (ISO). In the standard connector and receptacle arrangement, a port corresponding to each lead terminal connector end is formed in the header portion of the rhythm management device. When two or more leads are required, a separate receptacle is formed in the header for each corresponding lead's terminal connector end.

During the administration of certain pacing or defibrillation therapy it may be desirable to administer the same pacing therapy to two or more separate leads. For example, it may be desirable to transmit the same pacing signal through a left and right ventricular lead. In order to electrically couple the leads to a single receptacle of the cardiac rhythm management device, it is current practice to interconnect the right and left ventricular leads with a separate adapter and sleeve. The terminal connector ends of each lead plug into corresponding ports formed in the adapter. The adapter then plugs into a corresponding receptacle of the cardiac rhythm management device. Utilizing an adapter and sleeve to interconnect two or more leads increases the required number of sealing connections and overall size of the implanted device.

Fain et al. in U.S. Pat. No. 6,679,026 (the '026 device) describes a header adapter that provides at least one port in the header adapter that is sized differently than any of the header lead connector ports. The header adapter of the '026 device, in essence, is an in-line coupling to accommodate various sized lead terminal connector ends. The header adapter of the '026 device does not reduce the number of required header ports and further increases the number of required sealing connections. Hence, there is a need for an adapting member that interconnects two leads without increasing the required number of header ports or sealing connections. The present invention addresses these and other needs.

SUMMARY OF THE INVENTION

The purpose of the present invention is to provide an adapting member integrated into a main lead body, such that two leads may be electrically coupled together, thereby reducing the number of ports required in a corresponding header assembly of an implantable device. A terminal connector end of a unipolar lead may be coupled to the adapting member, such that a conducting wire of the unipolar lead is electrically coupled to a predetermined conducting wire of the main lead. The lead of the present invention includes an electrically insulating main body portion, at least one terminal connector, at least one electrode, at least one conductor, and the adapting member. The insulating main body, terminal connector, electrodes, and conductors may all be of a suitable construction known to those skilled in the art.

The lead of the present invention has a proximal and distal end, wherein terminal connectors are attached to the proximal end of the main body. The terminal connectors are adapted for coupling the terminal end of the lead to an implantable medical device. The lead may include one or more conductors for unipolar or bi-polar pacing and accordingly may include one or more terminal connectors electrically coupled to the proximal end of the conductors. The electrodes are embodied within a distal end portion of the main body portion and electrically connected to a distal end of each corresponding conductor.

The adapting member extends from the lead and may be formed as part of the electrically non-conducting main body portion of the lead. The adapting member includes a main housing having a port formed therein. The port has a terminal block engaged within the port and is adaptable for receiving and securing a terminal connector of the second lead thereto. A jumper wire is embedded within the adapting member and interconnects the terminal block contained within the port to a preselected one of the conductors insulated by the main body of the lead. When the terminal connector of the second lead is coupled to the terminal block, the preselected conductor of the main lead and the conductor of the second lead are electrically coupled in parallel. The jumper wire may include an outer electrically insulating layer, thereby further insulating the inner conductive wire.

The adapting member may extend from the lead adjacent the proximal end of the main body, such that the adapting member engages the header assembly of the implantable medical device when the lead is plugged into the header. When the adapting member engages the header assembly, the housing of the adapting member may have an aperture extending therethrough such that the aperture aligns with another header port of the implantable medical device. Alternatively, this aperture may be utilized to engage suturing material therethrough to thereby secure the adapting member to a desired location in the patient. Further, the adapting member may be contoured congruent with the shape of the header to form an overall continuous member of the implantable medical device.

OBJECTS

It is accordingly a principal object of the present invention to provide an adapting member integrated into a lead body, wherein two electrically interconnected leads may be coupled to a single port of a lead header assembly of an implantable device.

Another object of the present invention is to provide an adapting member integrated into a lead body capable of electrically coupling bi-polar and unipolar leads to a header assembly of an implantable device.

Yet another object of the present invention is to provide a lead that reduces the required overall size of the header assembly of the implantable medical device.

Still another object of the present invention is to provide an adapting member integrated into a lead body capable of coupling two leads to a single port of a header and providing a passage for a third lead terminal connector to pass through the adapting member and engage another port of the header assembly.

These and other objects as well as these and other features and advantages of the present invention will become readily apparent to those skilled in the art from a review of the following detailed description of the preferred embodiment especially when considered in conjunction with the accompanying drawings in which like numerals in the several views refer to corresponding parts.

DETAILED DESCRIPTION

Figure 1:
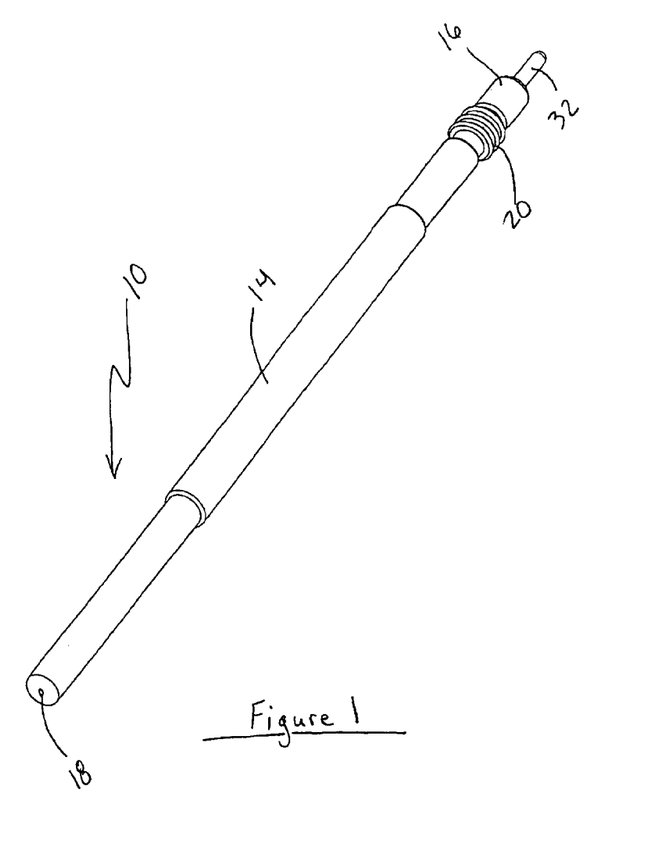
FIG. 1 is a fragmentary perspective view of a lead assembly of the present invention.
Figure 2:
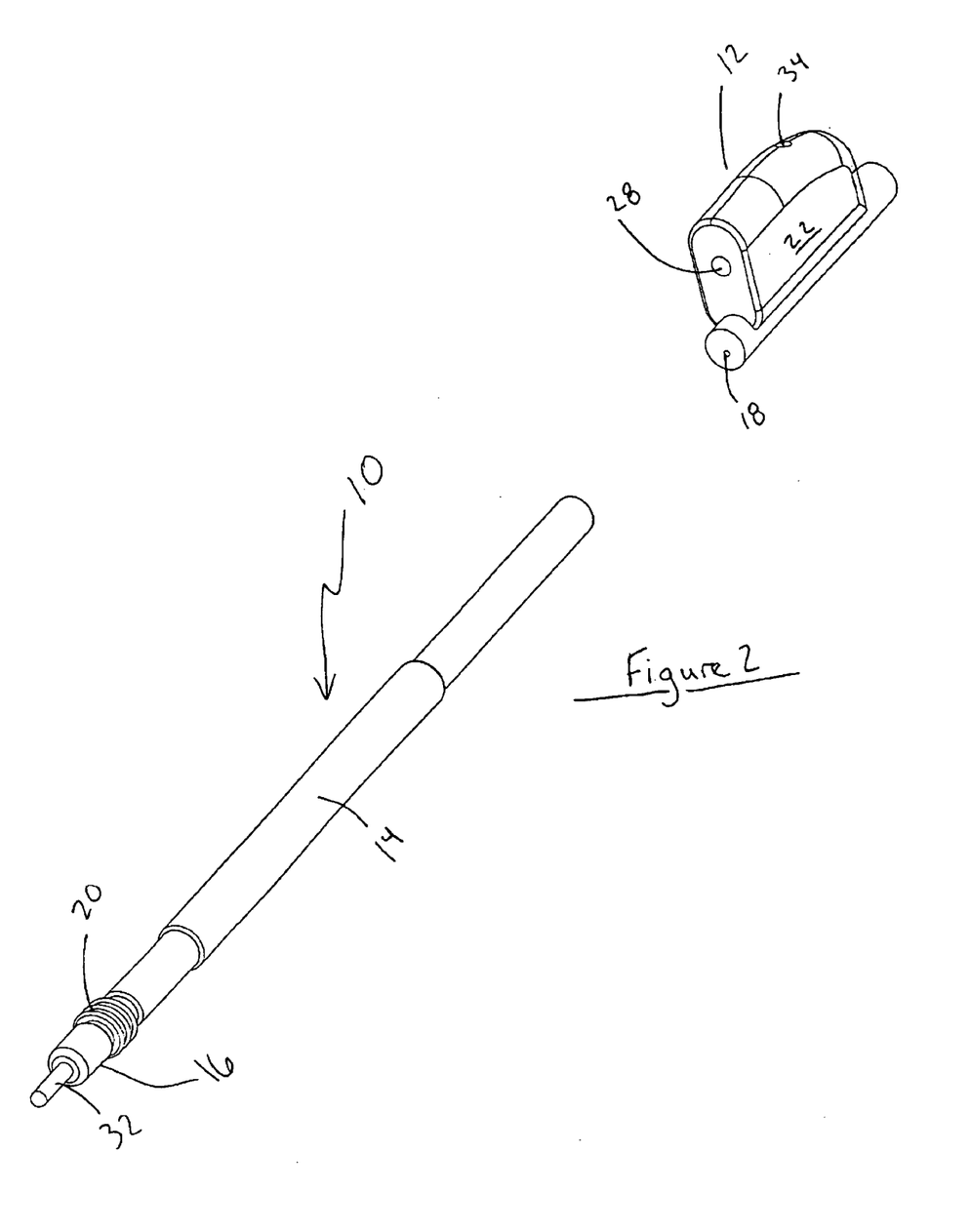
FIG. 2 is a rear fragmentary perspective view of the lead assembly of the type shown in FIG. 1.
Figure 3:
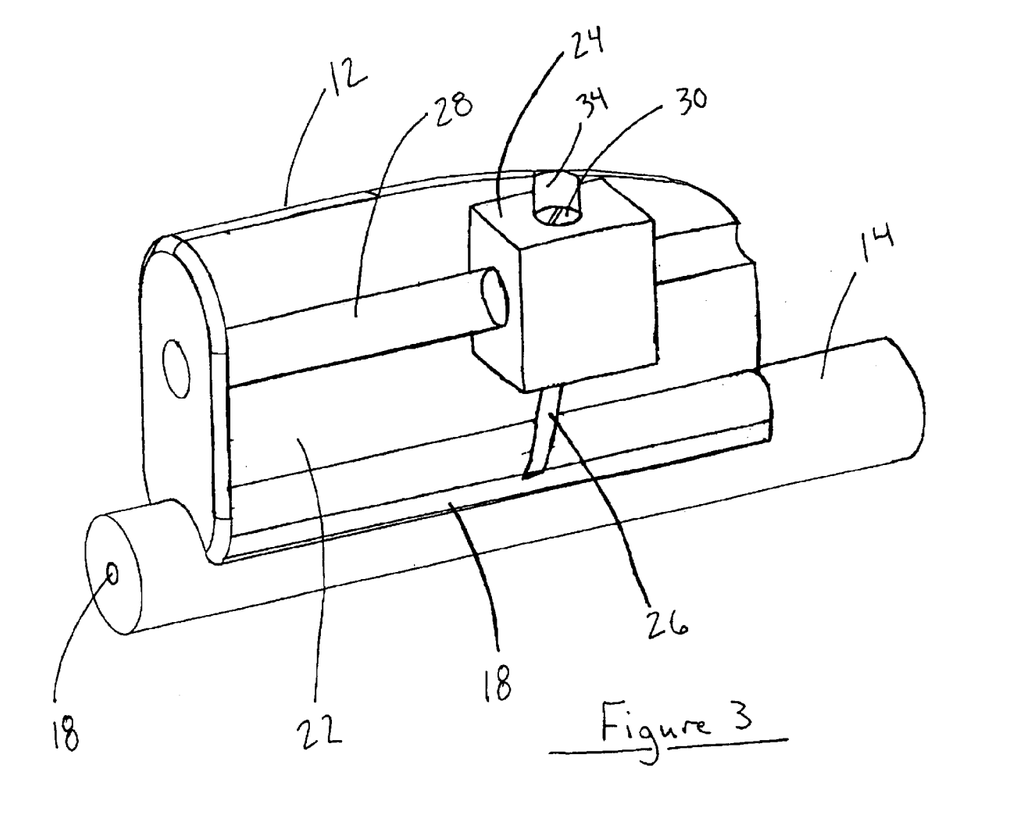
FIG. 3 is a fragmentary perspective view of the housing extending from the lead.
Figure 4:
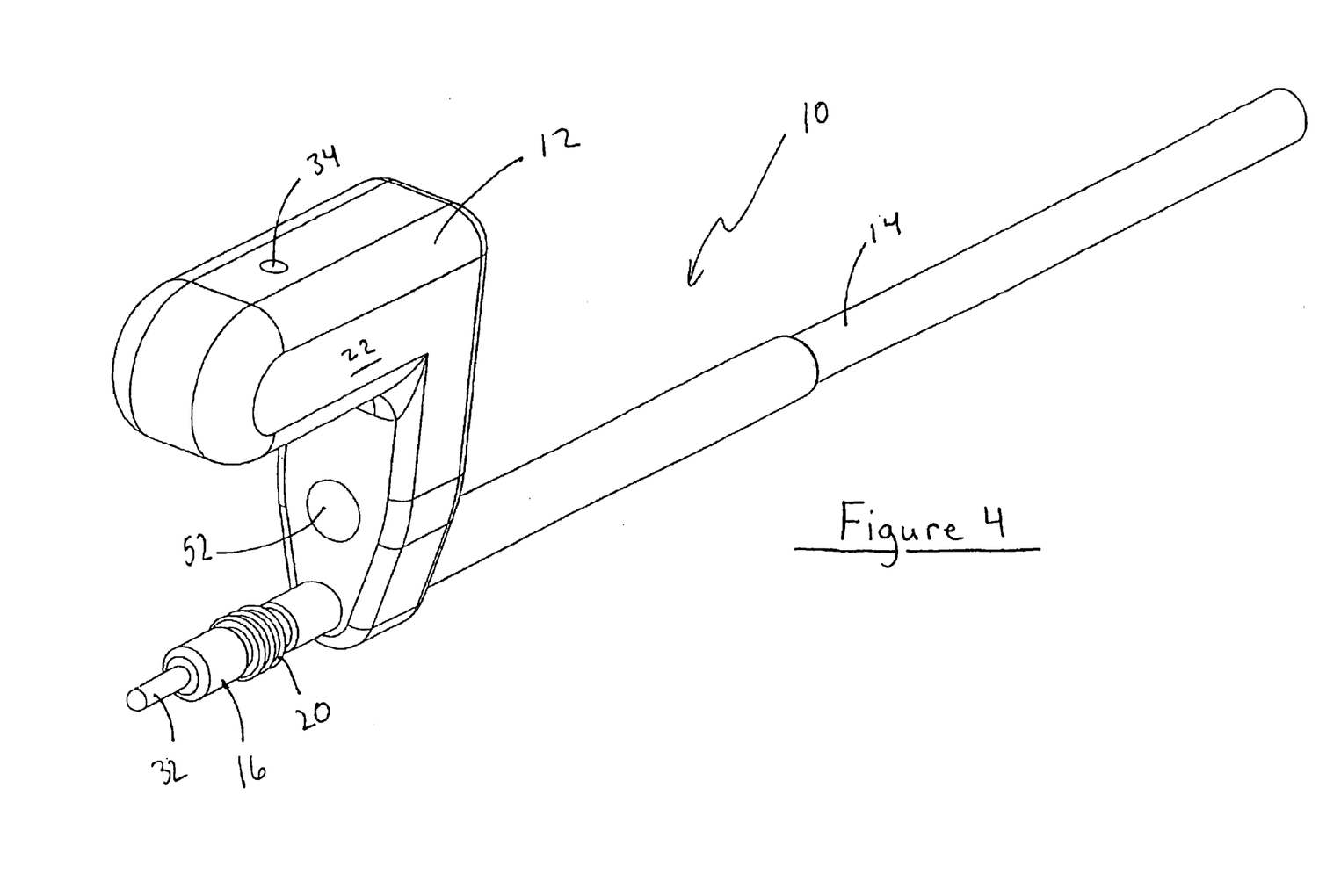
FIG. 4 is a fragmentary perspective view of an alternate embodiment of the lead assembly of the present invention.
Figure 5:
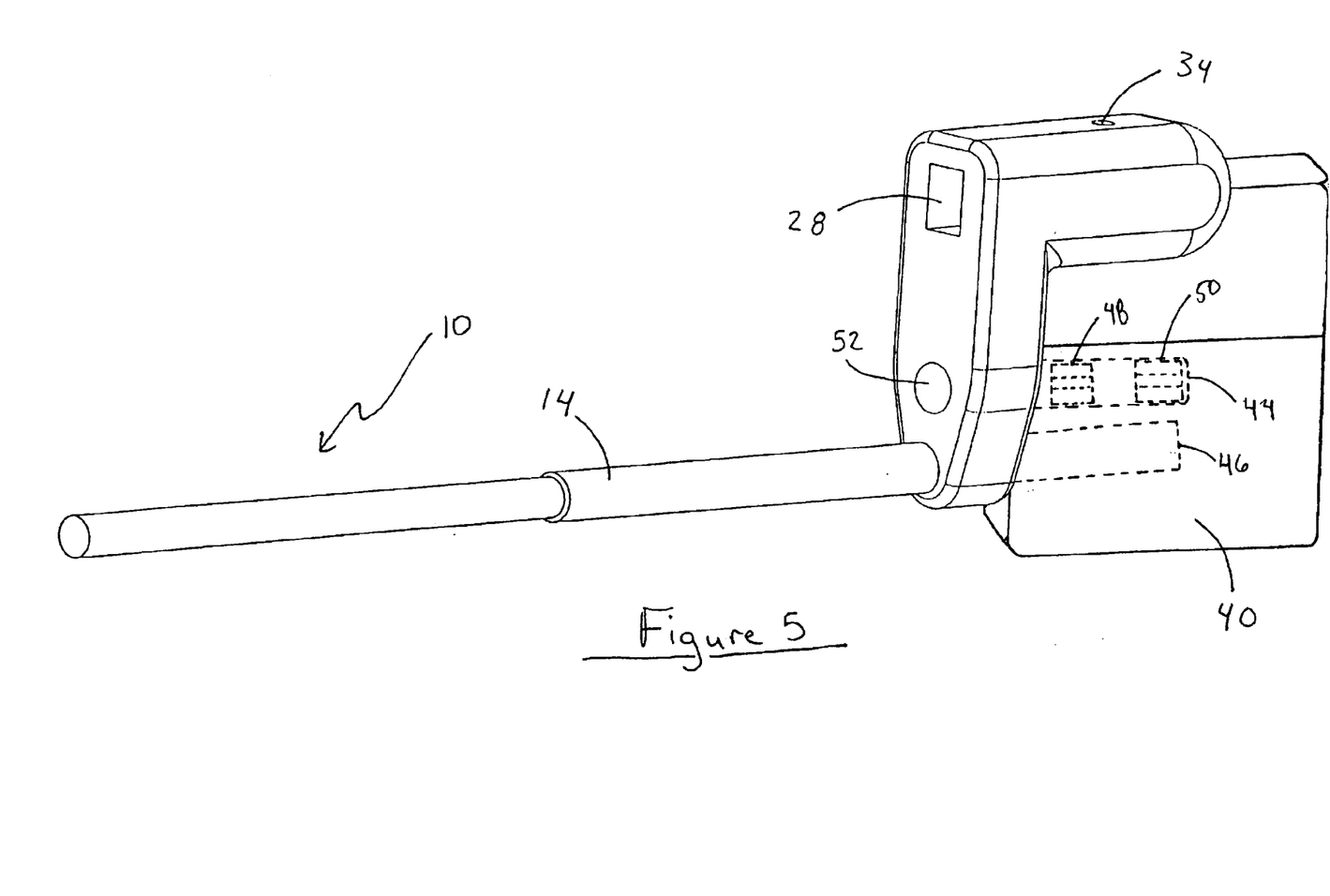
FIG. 5 is a fragmentary perspective view of the lead assembly engaged to a header and pulse generator of an implantable medical device with portions of the terminal connector omitted for clarity.
Figure 6:
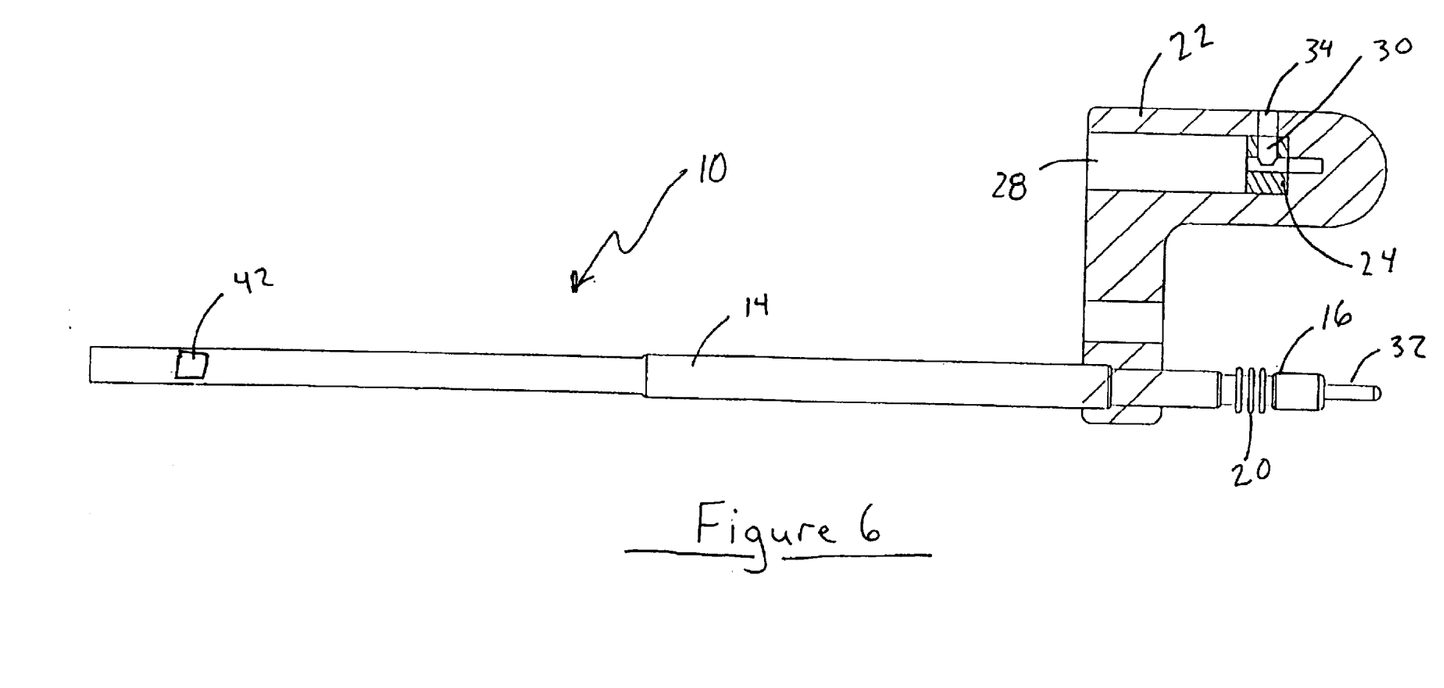
FIG. 6 is a partial sectional fragmentary side elevational view of the lead assembly of the type shown in FIG. 4.

Referring fist to FIGS. 1–3, a lead 10 of the present invention is generally shown. The lead 10 generally includes an adapting member 12, a non-conductive main body 14, at least one lead terminal connector 16, at least one electrode 42 (see FIG. 6), at least one conductor 18 and sealing members 20. The adapting member 12 includes a non-conductive housing 22, terminal block 24, jumper wire 26, port 28, and set screw 30. The housing 22 and main body 14 may be molded or otherwise constructed as a single, unitary member from the same non-conductive medical grade polymer of known suitable construction, silicone rubber being preferred. Without any limitation intended, the terminal blocks 24, terminal pin 32, conductor 18, and jumper wire 26 are manufactured from titanium or other conductive material sufficient to meet medical standards and all requirements of current transmission.

The housing 22 includes the terminal block 24 and jumper wire 26 embedded therein. The port 28 is formed in the housing 22 and extends from a first end of the housing 22 to an opposite end, intersecting the terminal block 24. The port 28 is adapted for sealably receiving a lead terminal connector of another lead, wherein the terminal pin of its terminal connector engages the terminal block 24. An aperture 34 is formed in the housing 22 extending from an external surface into the housing. The aperture 34 is aligned with a set screw 30 extending into the terminal block, wherein the set screw 30 retains the terminal pin of the other lead's terminal connector to the terminal block 24. When the set screw 30 is tightened, the second lead is held in place in contact with the corresponding terminal block 24, thereby insuring mechanical and electrical contact between the lead and terminal block 24. The jumper wire 26 is embedded within the adapting member and interconnects the terminal block 24 to the selected conductor 18. The jumper wire 26 is welded or otherwise attached for electrical conduction between the jumper wire 26 and terminal block 24. A seal plug (not shown) having a shape congruent with the aperture 34 and adaptable for sealable engagement with the housing 22 may be provided to sealably enclose the aperture 34. Of course those skilled in the art will appreciate that a medical adhesive or epoxy may alternatively be applied in the aperture 34 to thereby isolate the terminal block 24 from fluid contact. Those skilled in the art will appreciate that the port may be tapered or stepped having varying diameters to thereby fittingly receive the shape and size of the terminal end of the lead. The terminal connector 16 and pin 32 of the lead may manufactured in accordance with the International Organizations ISO standards.

Figure 7:
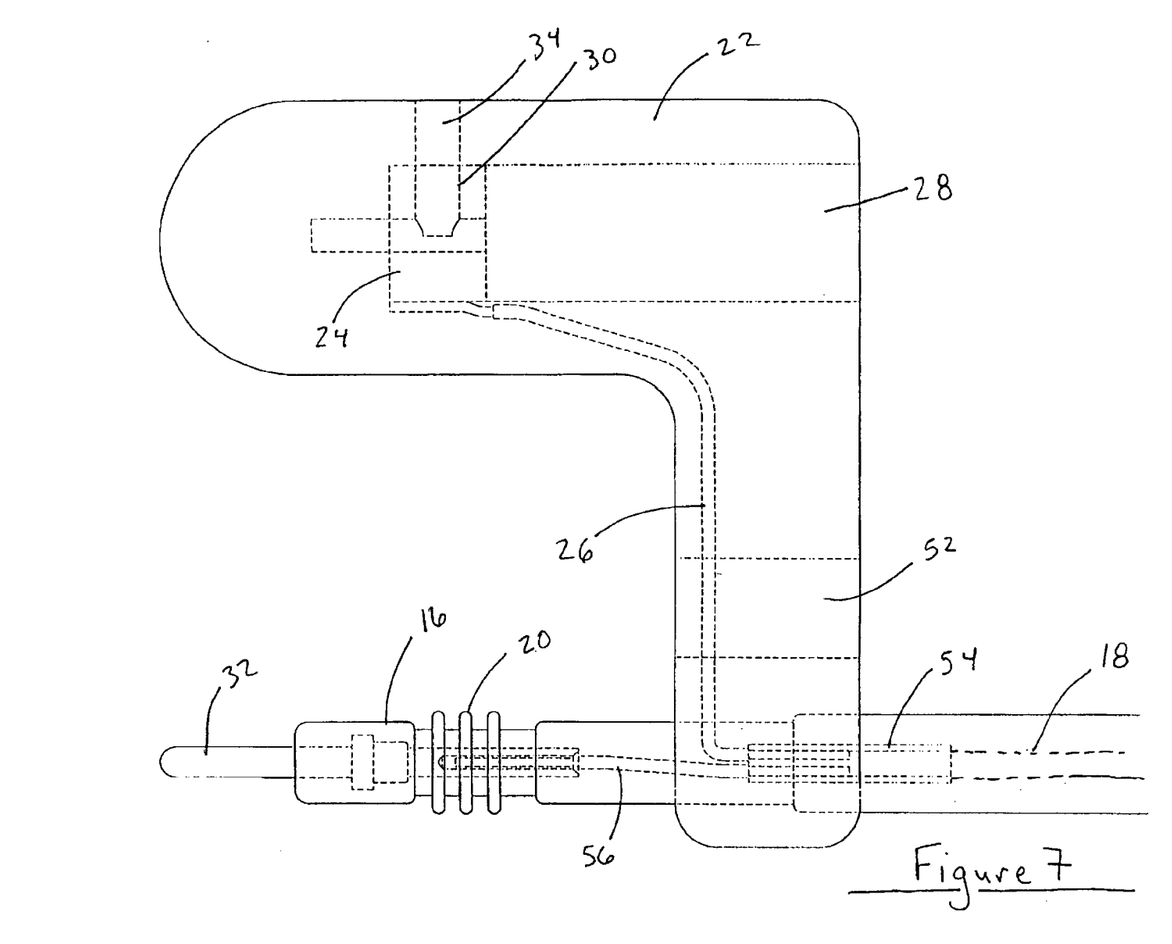
FIG. 7 is a partial sectional fragmentary side elevational view of the proximal end of the lead assembly of the type shown in FIG. 4.
Figure 8:
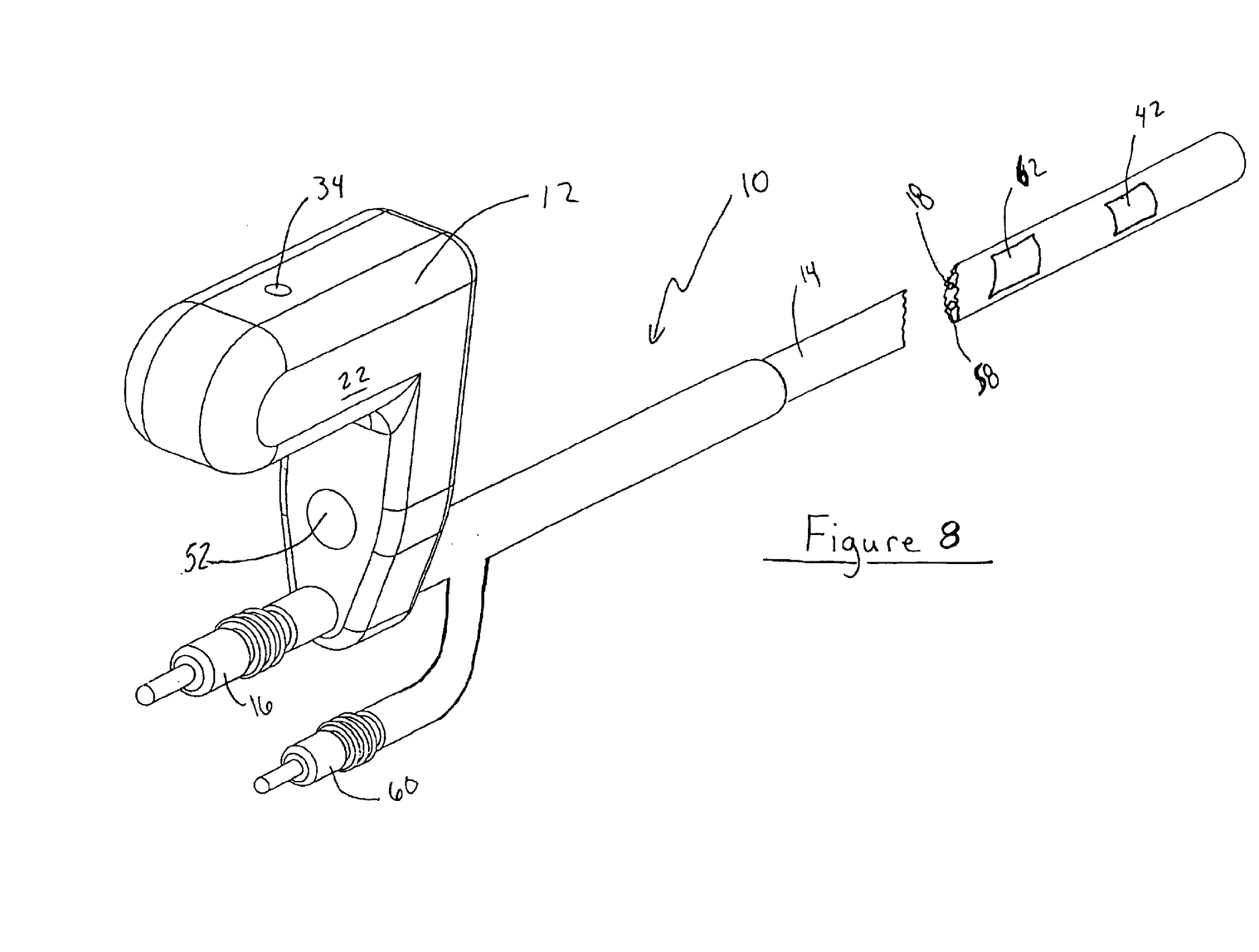
FIG. 8 is a partial sectional fragmentary perspective view of an alternate embodiment of the lead assembly of the present invention.

Referring next to FIGS. 4–7, an alternate embodiment of the present invention is shown. The lead 10 includes an adapting member 12 modified in shape to conform and engage the header 40 of the implantable device. The header is shown having two ports 44 and 46, wherein the port 44 is shown having two terminal blocks 48 and 50 suitable for electrically coupling a bi-polar lead of known suitable construction (see FIG. 5). A bore 52 extends through the housing 22 of the adapting member 12 and aligns with port 44 of the header 40. In this manner a terminal connector of another lead may be coupled to the header. As shown in FIG. 7, the adapting member 12 includes the jumper wire 26 embedded within the adapting member 12. A first end of the jumper wire 26 is welded or otherwise attached to the terminal block 24 for electrical conduction between the jumper wire 26 and terminal block 24. The other end of the jumper wire 26 is electrically coupled to junction block 54. The proximal end of the conducting wire 18 is also connected to the junction block 54. Further, a conducting wire 56 electrically couples the terminal pin 32 to the junction block 54. In this manner, both the terminal pin 32 and terminal block 24 are electrically coupled to the conducting wire 18. FIG. 8 shows yet another embodiment wherein the lead 10 includes a second electrode 62 coupled to a second conducting wire 58, which in turn is electrically coupled to a second terminal connector 60 in a known suitable manner.

Having described the constructional features of the present invention, the mode of use will next be presented. During the pacing of a patient's heart, it may be desirable to transmit simultaneously from a pulse generator an identical electrical signal through two or more leads electrically coupled to the pulse generator. For example, during CHF therapy it is believed that the left and right ventricles may be effectively paced by transmitting simultaneously the same pacing signal to both the left and right ventricle. The lead of the present invention may be utilized to electrically couple two or more leads to a single port of the pacing device, thereby allowing simultaneous transmission of an identical signal through the leads. Hence, independent pacing signals to the left ventricle and right ventricle leads would not be required to simultaneously pace the left and right ventricles.

Utilizing the lead 10 of the present invention, the terminal connector 16 of the lead is electrically coupled to the header assembly. This lead may be designated for pacing the right ventricle, for example. A terminal connector of a second lead designated for pacing the left ventricle, for example, is inserted into the port 28 of the adapting member 12 of the lead of the present invention. In this manner, the pacing signal transmitted through the terminal pin of the left ventricle lead will be the same as that transmitted to the terminal pin of the right ventricle lead.

This invention has been described herein in considerable detail in order to comply with the patent statutes and to provide those skilled in the art with the information needed to apply the novel principles and to construct and use such specialized components as are required. However, it is to be understood that the invention can be carried out by specifically different devices, and that various modifications, both as to the equipment details and operating procedures, can be accomplished without departing from the scope of the invention itself What is claimed is:

What is claimed is:

1. A lead capable of electrical and mechanical coupling to both a port of an implantable medical device's header assembly and to another lead, said lead comprising:
   (a) an elongated, main body portion having a proximal and distal end;
   (b) at least one terminal connector attached to the proximal end of the main body and adapted for coupling the lead to a header assembly of a medical device;
   (c) at least one electrode embodied within the main body portion;
   (d) at least one conductor corresponding with each electrode and electrically insulated, wherein a distal end of each conductor is attached to each corresponding electrode and a proximal end of each conductor is attached to at least one corresponding terminal connector;
   (e) an adapting member formed as a part of the main body portion and extending from the lead, the adapting member having a port adaptable for sealably receiving a terminal connector of a second lead, said port having an electrically conductive terminal block positioned within said port, wherein a jumper wire is electrically coupled to the terminal block and the conductors of the main body of the lead, said adapting member further including an aperture extending therethrough such that the aperture aligns with a header port when the lead is coupled to the header assembly.

2. The lead as recited in claim 1, wherein said adapting member is positioned on said lead adjacent to the proximal end of the main body.

3. The lead as recited in claim 1, wherein said port of said adapting member is suitable for receiving a terminal end of a uni-polar lead.

4. The lead as recited in claim 1, wherein said jumper wire includes an outer electrically insulating layer and an inner conductive wire.

5. The lead as recited in claim 1, wherein said adapting member engages the header assembly of the implantable medical device.

6. The lead as recited in claim 5, wherein said adapting member is contoured to conform to a shape of the header assembly.

7. A lead capable of electrical and mechanical coupling to both a port of a header assembly of an implantable medical device and to the terminal end of another lead, said lead comprising:
   (a) an elongated, main body portion having a proximal and distal end;
   (b) at least one terminal connector attached to the proximal end of the main body and adapted for coupling the lead to a header assembly of a medical device;
   (c) at least one electrode embodied within the main body portion;
   (d) at least one conductor corresponding with each electrode and electrically insulated, wherein a distal end of each conductor is attached to each corresponding electrode and a proximal end of each conductor is attached to a corresponding terminal connector;
   (e) an adapting member formed as an integral part of the main body portion and extending from said lead adjacent the proximal end of the main body, said adapting member having a port adaptable for sealably receiving a terminal connector of a second lead, said port having an electrically conductive terminal block positioned within said port, wherein a first end of a jumper wire is connected to a terminal block and a second end of said jumper wire is connected to one of the conductors of the main body of the lead, said adapting member having an aperture extending therethrough such that the aperture aligns with a header port when the lead is coupled to the header assembly.

8. The lead as recited in claim 7, wherein said port of said adapting member is adapted for receiving a uni-polar lead.

9. The lead as recited in claim 7, wherein said jumper wire includes an outer electrically insulating layer and an inner conductive wire.

10. The lead as recited in claim 7, wherein said adapting member engages the header assembly of the implantable medical device.

11. The lead as recited in claim 10, wherein said adapting member is contoured to conform to a shape of the header assembly.

* * * * *